United States Patent
Rao et al.

(10) Patent No.: US 8,252,549 B2
(45) Date of Patent: Aug. 28, 2012

(54) MULTI-PURPOSE SUBSTRATES USEFUL FOR CELL CULTURE AND METHODS FOR MAKING

(75) Inventors: Hongwei Hanna Rao, Horseheads, NY (US); Jian Tan, Ithaca, NY (US)

(73) Assignee: Corning Incorporated, Corning, NY (US)

( * ) Notice: Subject to any disclaimer, the term of this patent is extended or adjusted under 35 U.S.C. 154(b) by 351 days.

(21) Appl. No.: 12/625,952

(22) Filed: Nov. 25, 2009

(65) Prior Publication Data

US 2011/0124026 A1    May 26, 2011

(51) Int. Cl.
 *C12Q 1/04*    (2006.01)
(52) U.S. Cl. .......................... 435/34; 435/176
(58) Field of Classification Search .................. 435/176, 435/34
 See application file for complete search history.

(56) References Cited

U.S. PATENT DOCUMENTS

| | | | |
|---|---|---|---|
| 6,720,023 | B1 | 4/2004 | Kim et al. |
| 7,405,037 | B2 | 7/2008 | Greenwalt |
| 2002/0042657 | A1 | 4/2002 | Pugh et al. |
| 2005/0250171 | A1* | 11/2005 | Greenwalt ...................... 435/23 |
| 2008/0206831 | A1* | 8/2008 | Coffey et al. .................. 435/176 |
| 2011/0294142 | A1* | 12/2011 | Lahiri et al. .................. 435/7.23 |
| 2011/0294151 | A1* | 12/2011 | Rao et al. ........................ 435/29 |

FOREIGN PATENT DOCUMENTS

| | | |
|---|---|---|
| WO | 01/82773 | 11/2001 |
| WO | 2008/103339 A2 | 8/2008 |

OTHER PUBLICATIONS

Hanagata, N., et al., "Phenotype and gene expression pattern of osteoblast-like cells cultured on polystyrene and hydroxyapatite with pre-adsorbed type-I collagen", Journal of Biomedical Materials Research. Part A, vol. 83, No. 2, Nov. 2007, pp. 362-371.
Yang, X. B., et al. "Biomimetic collagen scaffolds for human bone cell growth and differentiation", Tissue Engineering, vol. 10, No. 7-8, Jul. 2004, pp. 1148-1159.
Bernards, M. T., et al., "MC3T3-E1 cell adhesion in hydroxyapatite with adsorbed bone sialoprotein, bone osteopontin, and bovine serum albumin", Colloids and Surfaces., B, Biointerfaces, vol. 64, No. 2, Jul. 15, 2008, pp. 236-247.
http://www.boneandjointburden.org, 2008.
Boyle et al; "Osteoclast Differentation and Activation"; Nature, 2003, 423:337-343.
Schwartz et al; "Osteoblast Proliferation and Differentiation on Dentin Slices Are Modulated by Pretreatment of the Surface With Tetracycline or Osteoclases"; J. Periodontol, 2000, 71(4):586-97.
Berger et al; "Scanning Electrochemical Microscopy At the Surface of Bone-Resorbing Osteoclasts: Evidence for Steady-State Disposal and Intracellular Function Compartmentalization of Calcium"; J Bone Miner Res. 200, 16(11):2092-102, 2001.
Osteoassay Human Bone Plate TM, Sold by Lonza, 2008.

* cited by examiner

*Primary Examiner* — Ralph Gitomer
(74) *Attorney, Agent, or Firm* — Susan S. Wilks (57) ABSTRACT

Described herein are multi-purpose substrates composed of (1) a base coated with a calcium phosphate coating and (2) a fluorophore-labeled collagen adsorbed on the calcium phosphate coating. The multi-purpose substrates are useful in culturing and studying the activity of a variety of cells. The multi-purpose substrates described herein can be used for both solution- and image-based analysis of cultured cells. New methods for producing and using such coated substrates are also disclosed.

17 Claims, 3 Drawing Sheets

MULTI-PURPOSE SUBSTRATES USEFUL FOR CELL CULTURE AND METHODS FOR MAKING

BACKGROUND

Culturing of adherent animal cells is generally carried out by seeding a substrate with cells in the presence of a biological medium. The cell culture substrate and medium are important in providing an environment in which cells adhere and function in a manner similar to in vivo. The culturing of cells can provide a research tool for studying a number of different types of diseases and possible drugs for treating or preventing these diseases.

When cells are cultured on the surface of a substrate, the cells can be imaged by an optical microscope. Image based analysis, however, is tedious and not in real time. For example, in the case of bone cells, the cell culture has to be stopped and bleached to reveal the pits formed on the surface of the substrate. Thus, in addition to surface imaging, it would be desirable to have a substrate that permits additional detection techniques when cells are cultured on the substrate. Described herein are multi-purpose substrates and methods for producing the same that address these needs.

SUMMARY

In accordance with the purposes of the disclosed compositions, articles, and methods, as embodied and broadly described herein are multi-purpose substrates composed of (1) a base coated with a calcium phosphate coating and (2) a fluorophore-labeled collagen adsorbed on the calcium phosphate coating. The multi-purpose substrates are useful in culturing and studying the activity of a variety of cells. The multi-purpose substrates described herein can be used for both solution- and image-based analysis of cultured cells. New methods for producing and using such coated substrates are also disclosed.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying figures, which are incorporated in and constitute a part of this specification, illustrate several aspects described below.

DETAILED DESCRIPTION

The materials, compounds, compositions, articles, devices, and methods described herein may be understood more readily by reference to the following detailed description of specific aspects of the disclosed subject matter and the Examples included therein and to the Figures.

Before the present materials, compounds, compositions, articles, devices, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting. Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, and reference to "a precursor" includes mixtures of two or more such precursors.

"Optional" or "optionally" means that the subsequently described event or circumstance can or cannot occur, and that the description includes instances where the event or circumstance occurs and instances where it does not.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers or prepared by methods known to those skilled in the art.

Reference will now be made in detail to specific aspects of the disclosed materials, compounds, compositions, articles, and methods, examples of which are illustrated in the accompanying Examples and Figures.

Described herein are multi-purpose substrates composed of (1) a base coated with a calcium phosphate coating and (2) a fluorophore-labeled collagen adsorbed on the calcium phosphate coating. Each component of the substrate as well as methods for making and using the substrates is described in detail below.

The term "base" as used herein is any article having a surface where calcium phosphate can be coated. In one aspect, the substrate can possess one or more wells or depressions that can receive and hold a solution that can produce a calcium phosphate coating. The base can assume many shapes and sizes depending upon the desired end-use of the multi-purpose substrate. For example, the base can be a microwell plate having a plurality of wells with varying diameters and heights.

The base can be prepared from a variety of different materials. In one aspect, the base comprises a polymer. Examples of such polymers include, but are not limited to homopolymers and copolymers of a polyester, a polyvinylchloride, a polyvinylidene fluoride, a polytetrafluoroethylene, a polycarbonate, a polyamide, a poly(meth)acrylate, a polystyrene, a polyethylene, polypropylene, or an ethylene/vinyl acetate copolymer. Blends of polymers are also known and may also be considered for this application. These blends may include, but are not be limited to commercially available materials such as polycarbonate/ABS, PVC/ABS, polyphenyleneoxide and high impact polystyrene, but also may include novel blends of the homopolymers and copolymers listed above. These polymers can be formed into cell culture vessels including wells, multi-well plates, flasks, and the like. In addition, the cell culture container may be a virtual well formed from a bottom base, such as a glass slide, or a sheet of polymer material, with a structure placed upon the bottom base in a water-impermeable manner, to form sidewalls of a cell culture well.

In one aspect, the polymeric base can be modified prior to applying the calcium phosphate coating. The polymeric base can be modified to change the charge of the base, to include active chemical moieties, or to increase the amount of surface oxygen. For example, the surface of the base can be exposed to energy such as corona discharge, plasma treatment (e.g., ammonia, nitrogen, oxygen, nitrous oxide, carbon dioxide, air, or other gases that can be activated or ionized), heat, ultraviolet radiation, gamma radiation, UV ozone, or microwave energy. The increase in surface oxygen increases the hydrophilic nature of the base, which can be desirable in certain aspects. The treatment of the base surface can also modify the overall surface charge on the base, which can facilitate coating the surface with calcium phosphate. In one aspect, the base comprises polystyrene that has been treated to increase the amount of surface oxygen.

In another aspect, the base comprises an inorganic material. Examples of inorganic materials include metals and semiconductor materials that can be surface oxidized, glass, and ceramic materials. Examples of metals that can be used as base materials are oxides of aluminum, chromium, titanium and steel. Semiconductor materials used for the base material can include silicon and germanium. Glass and ceramic materials used for the base material can include quartz, glass, porcelain, alkaline earth aluminoborosilicate glass, soda lime silicate glass and other mixed oxides. Further examples of inorganic substrate materials include zinc compounds, mica, silica and inorganic single crystal materials. It is contemplated that the base can include be a layered system, any of the polymeric or inorganic materials described above can be coated on each other. For example, the base can be a polymeric surface coated with silica.

The base with a calcium phosphate coating on the surface of the base is referred to herein as "the pre-substrate." The pre-substrate can be prepared by a variety of techniques. For example, the base can be contacted with a solution comprising a plurality of precursor components for producing the calcium phosphate coating. The method of contacting the base with the solution varies with the selection of the base. For example, when the base is a glass slide, the slide can be adhered to a gasket (e.g., flexiPerm reusable cell culture chamber manufactured by Greiner Bio One, Germany), and the solution is added to the wells. In another aspect, when the base is a microwell plate, each well is filled with a specific amount of solution. In this aspect, it is contemplated that each well is filled with the same or different solution (i.e., different precursor components and/or different amounts of precursor components). The amount of solution added to each well can vary, and will depend upon the size of the well (diameter and height), the material of the base, and the concentration of the precursor components. In one aspect, each well is partially filled with the solution. Another technique for contacting the base with the solution is spray coating.

The precursor component is any component that can result in the formation of a calcium phosphate coating on the surface of the base. Although the precursor component is generally a salt, the precursor component can be an acid or base as well. In one aspect, the precursor component comprises an alkali metal halide, an alkali metal sulfate, an alkali metal carbonate, an alkali metal phosphate, an alkaline earth metal halide, an alkaline earth metal sulfate, an alkaline earth metal carbonate, an alkaline earth metal phosphate, or any combination thereof. It is intended that carbonate also includes bicarbonate phosphate also includes hydrogen and dihydrogen phosphate, and sulfate also includes hydrogen sulfate.

In another aspect, the precursor component comprises any combination of calcium chloride, magnesium chloride, sodium bicarbonate, potassium hydrogen phosphate, sodium phosphate, and sodium chloride. The ions of these components are generally present in blood plasma. Thus, solutions comprising these components are generally referred to as simulated body fluids or SBF. The production of simulated body fluids or derivatives thereof is known in the art. The SBF solutions can be modified. For example, in certain aspects, the solution does not require potassium or sulfur.

The concentration of precursor components present in the solution can vary. In certain aspects, the concentration is the maximum amount of precursor components that are soluble in water alone or in combination with minor amounts of other solvents (e.g., an alcohol) or pH modifiers (e.g., acids or bases). In one aspect, the solution comprises SBF. In another aspect, the solution comprises 5× or 10×SBF. The initial pH of the solution can also vary with the concentration of precursor components, the material of the base, and the surface charge (if any) on the base surface. In one aspect, the solution has an initial pH of from 3 to 8, 3 to 7, 3 to 6, 4 to 8, 5 to 8, 5 to 7, or 5 to 6. By varying the pH of the solution, it is possible to control the overall morphology of the calcium phosphate coating formed on the base.

As discussed above, in certain aspects the base can be treated with a number of surface techniques to change the surface charge of the base, which in turn can influence surface wettability. For example, when the surface of the base is treated to increase the amount of oxygenated groups (e.g., hydroxyl, carboxyl), the treated base may have a greater affinity for the solution. Another consideration is the amount of solution used. In general, the volume of solution is sufficient to produce a suitable calcium phosphate coating. The amount of solution used depends on the concentration of the solution and the desired thickness of the coating.

After the base has been contacted with the solution, the base is incubated to produce the calcium phosphate coating on the surface of the base. The temperature and duration of incubation can vary depending upon the desired morphology of the calcium phosphate coating on the base. For example, it may be desirable to have a longer incubation time at a lower temperature to produce smaller calcium phosphate crystals on the surface of the base. In one aspect, the incubation step is performed at a temperature up to 90° C. for up to 72 hours.

In another aspect, the incubation step is performed at a temperature from room temperature to 90° C., 30° C. to 80° C., or 40° C. to 60° C. from 1 to 72 hours, 2 to 36 hours, 2 to 24 hours, or 2 to 18 hours.

Depending upon the selection of the precursor components, gases can be produced during incubation and crystallization. For example, if the solution comprising the precursor components is acidic and bicarbonate is added to the solution, $CO_2$ gas is produced. Not wishing to be bound by theory, the removal of the gas can influence the pH of the solution, which in turn can influence the rate and amount of crystal formation. Depending upon the components present in the solution, crystal formation may be sensitive to changes in pH. For example, when bicarbonate is added to an acidic solution, $CO_2$ is generated. If $CO_2$ is removed from the system, the equilibrium is shifted to the right and more acid in solution is removed (i.e., reacts with bicarbonate). This results in an increase in pH. If $CO_2$ is not removed, an equilibrium is reached, and no further change in acid concentration and pH occurs (i.e., bicarbonate does not react any further with the acid). Thus, where crystal growth on the base is sensitive to the pH of the solution, removal of any gases generated during incubation can be performed to promote crystal formation.

In other aspects, when the base comprises a series of bases (e.g., a stack of microplates or Petri dishes), during incubation a slight vacuum can be applied to remove gas from the stacked system. In the alternative, the stacked system can be arranged such that the each plate or dish is loosely stacked so that any gases generated during incubation can escape.

After the incubation step, the base has a calcium phosphate coating. Subsequent steps can be performed on the coated base including washing the pre-substrate with water, drying the pre-substrate by applying a stream of air or heating the pre-substrate.

The thickness of the calcium phosphate coating on the base can vary depending upon the base to be coated as well as the nature and concentration of precursor components selected. For example, the thickness of the coating ranges from 200 nm to 800 nm, 200 nm to 700 nm, 200 nm to 600 nm, 200 nm to 500 nm, 200 nm to 400 nm, 300 nm to 800 nm, 400 nm to 800 nm, 500 nm to 800 nm, or 600 nm to 800 nm. If thicker coatings are desired, the contacting and incubation steps described above can be performed multiple times sequentially to produce thicker coatings. In certain aspects, thinner coatings are desirable (e.g., less than one micron) in order to better visualize the cells on the substrate and improve sensitivity to cell resorption.

The base can be coated with calcium phosphate in a variety of patterns and designs. For example, a removable adhesive tape or mask can be placed on the surface of the base to produce a pattern or design of exposed substrate that ultimately will be coated with calcium phosphate. The tape or mask is then removed after incubation and crystal formation. Alternatively, if the base is to be treated in order to increase surface oxygen, prior to surface treatment, a removable adhesive tape or mask can be placed on the surface of the base. Here, the calcium phosphate coating forms only on the portions or section of the base that have been surface treated, or if crystals form on masked areas they are more easily removed during subsequent washing steps.

In one aspect, the calcium phosphate coating comprises hydroxyapatite, which has the formula $Ca_5(PO_4)_3OH$. In another aspect, the calcium phosphate coating is composed of a substituted hydroxyapatite. A substituted hydroxyapatite is hydroxyapatite with one or more atoms substituted with another atom. The substituted hydroxyapatite is depicted by the formula $M_5X_3Y$, where M is Ca, Mg, Na; X is $PO_4$ or $CO_3$; and Y is OH, F, Cl, or $CO_3$. Minor impurities in the hydroxyapatite structure may also be present from the following ions: Zn, Sr, Al, Pb, Ba. In another aspect, the calcium phosphate comprises a calcium orthophosphate. Examples of calcium orthophosphates include, but are not limited to, monocalcium phosphate anhydrate, monocalcium phosphate monohydrate, dicalcium phosphate dihydrate, dicalcium phosphate anhydrous, octacalcium phosphate, beta tricalcium phosphate, alpha tricalcium phosphate, super alpha tricalcium phosphate, or tetracalcium phosphate. In certain aspects, the calcium phosphate coating includes crystals possessing carbonate groups ($CO_3$), which can facilitate adhesion of certain types of cells such as, for example, bone cells, during culturing. In other aspects, the calcium phosphate coating can also include calcium-deficient hydroxyapatite, which can preferentially adsorb proteins useful in cell culturing such as bone matrix proteins.

The calcium phosphate coatings produced generally have a high surface area and pore volume. The calcium phosphate coating is generally uniform on the surface of the base, which is desirable for cell culturing. Moreover, when the calcium phosphate coating has a uniform thickness, it enables better evaluation of adherent cells.

In one aspect, the pre-substrate is produced by the method comprising:
(a) introducing a base into a solution comprising a plurality of precursor components for producing a calcium phosphate coating on the surface of the base;
(b) inverting the base relative to the solution; and
(c) incubating the inverted base to produce the calcium phosphate coating on the surface of the base, wherein gas generated during incubation is permitted to escape.

The methods disclosed in International Publication No. WO 2008/103339, which are incorporated by reference in their entirety, can be used in this aspect. In this aspect, once the base has been contacted with the solution, the base is inverted relative to the solution. For example, when the base is a microwell or a slide adhered to a gasket, the base can be inverted 180°.

In certain aspects, the pre-substrate is exposed to gamma irradiation prior to adsorbing the fluorophore-labeled collagen to the pre-substrate.

The multi-purpose substrates described herein have fluorophore-labeled collagen adsorbed on the calcium phosphate coating of the pre-substrate. The term "adsorbed" as used herein with respect to the fluorophore-labeled collagen is defined as the non-covalent attachment or bonding of the fluorophore-labeled collagen to the calcium phosphate coating. The fluorophore-labeled collagen is neither directly nor indirectly covalently bonded to the calcium phosphate coating. The calcium phosphate coating is not modified in any way so that is can form a covalent bond with the fluorophore-labeled collagen. For example, the fluorophore-labeled collagen is not derivatized with linkers or spacers such as carbodiimides (e.g., 1-ethyl-3-[dimethylaminopropyl] carbodiimide hydrochloride), maleimides, or iodoacetyl groups, which can potentially form covalent bonds with functional groups present on the calcium phosphate coating.

A wide variety of fluorophores can be used in the fluorophore-labeled collagen. The fluorophore can be covalently or non-covalently bound to the collagen. In one aspect, the fluorophore is a lanthanide chelate. Examples of lanthanide chelates useful herein include, but are not limited to, β-diketone chelates of cerium, praseodymium, neodymium, promethium, samarium, europium, gadolinium, terbium, dysprosium, holmium, erbium, thulium, or ytterbium. Suitable β-diketones are, for example, 2-naphthoyltrifluoroacetone (2-NTA), 1-naphthoyltrifluoroacetone (1-NTA), p-methoxybenzoyltrifluoroacetone (MO-BTA), p-fluorobenzoyltrifluoroacetone (F-BTA), benzoyltrifluoroacetone (BTA), furoyltrifluoroacetone (FTA), naphthoylfuroylmethane (NFM), dithenoylmethane (DTM), and dibenzoylmethane (DBM). In one aspect, the lanthanide chelate is $Eu^{3+}$—N'-(p-isothiocyanatobenzyl) diethylenetriamine-$N^1,N^2,N^3$-tetraacetic acid (Perkin-Elmer).

In another aspect, the fluorophore can be Alexa Fluor 350, Alexa Fluor 488, Alexa Fluor 546, Alexa Fluor 555, Alexa Fluor 594, Alexa Fluor 647, Alexa Fluor 680, fluorescein isothiocyanate (FITC), Rhodamine 110, Rhodamine 123, Rhodamine 6G, Rhodamine Green, Rhodamine Red, and Rhodamine B. In other aspects, the fluorophore can be quantum dots, which are semiconductor nanocrystals with size-dependent optical and electronic properties.

The type of collagen in the fluorophore-labeled collagen is not limited to any particular type of collagen. For example, collagen types I, II, III, IV, V, VI, VII, VIII, VIX, or X, etc. can be used herein. The collagen can be recombinant or naturally occurring collagen. In one aspect, the collagen can be vertebrate collagen. In another aspect, the collagen is mammalian collagen such as, for example, human collagen. The type of collagen that is used can vary depending upon the cultured cell type. For example, when osteoclasts or osteoclast precursors are to be assayed, type I collagen can be used in the fluorophore-labeled collagen. Sources of type I collagen include rat tail collagen, bovine dermis collagen, human placental collagen, and kangaroo tail collagen. Alternatively, when tumor cells are to be assayed, type IV collagen can be used. Sources of type IV collagen include human or other mammalian placental collagen and Engelbreth-Holm-Swarm mouse sarcoma collagen.

The collagen can be purified as needed. It is desirable that the collagen be relatively pure so that detected fluorescence reflects true collagen degradation and not degradation of impurities. In one aspect, the collagen is at least about 90% pure, at least about 95% pure, or close to 100% pure.

The adsorption of the fluorophore-labeled collagen to the pre-substrate does not require special techniques or handling. For example, the pre-substrate can be immersed in a solution containing the fluorophore-labeled collagen. The temperature and duration of the adsorption step can vary depending upon the concentration of the fluorophore-labeled collagen and the desired thickness of the fluorophore-labeled collagen that is to be adsorbed on the pre-substrate. In one aspect, the adsorbing step is performed at 0° C. to 60° C. from 1 to 4 hours. In another aspect, the amount of the fluorophore-labeled collagen adsorbed to the calcium phosphate coating is from 5 μg/cm$^2$ to 1 mg/cm$^2$. After the fluorophore-labeled collagen has been adsorbed to the pre-substrate, the multi-purpose substrate can be subsequently washed and dried. Exemplary procedures for adsorbing the fluorophore-labeled collagen to the pre-substrate are provided in the Examples section.

The multi-purpose substrates described herein can be used to culture cells. The term "multi-purpose" as used herein refers to the ability of the substrates to permit multiple types of imaging and analysis of the cultured cells. For example, the multi-purpose substrates described herein can be used for both solution- and image-based analysis of cultured cells. Each of these techniques is described in detail below. The multi-purpose substrates also provide high throughput cell activity assays in real time. Therefore, both solution- and image-based assays can be performed with one substrate, which ultimately reduces material and labor costs.

The multi-purpose substrates described herein are useful in evaluating the activity of a cell or cell precursor. In one aspect, the method comprises
(a) culturing cells or cell precursors in a culture medium on the multi-purpose substrate;
(b) imaging the cells or cell precursors present on the multi-purpose substrate; and/or
(c) detecting the presence or absence of a fluorescence signal in a sample of culture medium.

The term "activity" is defined herein as any property, function, or mechanism of the cultured cells or cell precursors that can be qualitatively and/or quantitatively measured using the methods described herein. For example, the activity can be the ability of the cells to form resorption pits on the calcium phosphate coating of the multi-purpose substrate. Resorption pits are formed when a cell such as, for example, osteoclasts release hydrogen ions that may dissolve the calcium phosphate coating. Upon dissolution, the cell forms a pit or indentation in the calcium phosphate coating, which can be imaged by SEM or optical microscopy. The ability to effectively quantify the resorption pits (e.g., pit area, number of pits, etc.) is one way to evaluate the ability of cells to adhere and resorb to the multi-purpose substrate. In other aspects, the multi-purpose substrates can be used to evaluate the ability of cancer cells to degrade collagen on the surface of the substrate by monitoring using the fluorophore signal over time.

In addition to imaging cells adhered to the multi-purpose substrate, the multi-purpose substrate can be used for solution-based detection. Not wishing to be bound by theory, when the cell comes into contact with the fluorophore-labeled collagen, labeled collagen fragments are produced and released into solution. The fluorophore-labeled collagen fragments can be detected by methods known in the art for detecting the particular fluorophore used. For example, if the collagen is labeled with fluorescein, its fluorescence can be detected by use of a fluorimeter with excitation and emission wavelengths of 485 and 535 nm, respectively. Other fluorophores will have their own unique excitation and emission maxima, and these are known in the art. Some types of fluorophores, such as quantum dots, can be imaged by use of image analysis systems that detect fluorescence.

In the case when the fluorophore is a lanthanide chelate, the fluorescence produced by the lanthanide chelate can be measured without dissociating the lanthanide ion from the chelate. Alternatively, a low pH enhancement solution can be used to dissociate the lanthanide label from the labeled collagen. Here, free lanthanide (e.g., $Eu^{3+}$, $Sm^{3+}$, $Tb^{3+}$, $Dy^{3+}$) forms a stable, fluorescent chelate with components of the enhancement solution within a protective micelle. In one aspect, the enhancement solution can contain a suitable detergent such as Triton X-100, and a β-diketone to amplify the fluorescence after the separation. In certain aspects, in order to further improve the fluorescence, especially in aqueous solutions, a synergistic compound such as a Lewis base can be added. Suitable synergistic compounds include N-heterocyclic compounds (e.g., o-phenanthroline), as well as phosphines and phosphine oxides (e.g. trioctylphosphineoxide).

Fluorescence can be detected by time delay methods, which can reduce or eliminate the contribution of non-specific background fluorescence. For example, time-resolved fluorimetry can be used. Devices suitable for carrying out time-resolved fluorimetry include, but are not limited to, a Victor spectrofluorimeter (e.g., Victor or Victor$^{2TM}$ from EG&G Wallac), SPECTRAmax GEMINI (Molecular Devices), the LJL-Analyst, and FLUOstar from BMG Lab Technologies.

Many types of cells can be cultured on the multi-purpose substrate including, but not limited to, stem cells, committed stem cells, differentiated cells, and tumor cells. Examples of stem cells include, but are not limited to, embryonic stem cells, bone marrow stem cells and umbilical cord stem cells. Other examples of cells used in various embodiments include, but are not limited to, myoblasts, neuroblasts, fibroblasts, glioblasts, germ cells, hepatocytes, chondrocytes, keratinocytes, smooth muscle cells, cardiac muscle cells, connective tissue cells, glial cells, epithelial cells, endothelial cells, hormone-secreting cells, cells of the immune system, and neurons. In one aspect, bone cells such as osteoclasts, osteocytes, and osteoblasts can be cultured with the multi-purpose substrates described herein.

Cells useful herein can be cultured in vitro, derived from a natural source, genetically engineered, or produced by any other means. Any natural source of prokaryotic or eukaryotic cells can be used.

Atypical or abnormal cells such as tumor cells can also be used herein. Tumor cells cultured on the multi-purpose substrates can provide more accurate representations of the native tumor environment in the body for the assessment of drug treatments. Growth of tumor cells on the multi-purpose substrates described herein can facilitate characterization of biochemical pathways and activities of the tumor, including gene expression, receptor expression, and polypeptide production, in an in vivo-like environment allowing for the development of drugs that specifically target the tumor.

Cells that have been genetically engineered can also be used herein. The engineering involves programming the cell to express one or more genes, repressing the expression of one or more genes, or both. Genetic engineering can involve, for example, adding or removing genetic material to or from a cell, altering existing genetic material, or both. Embodiments in which cells are transfected or otherwise engineered to express a gene can use transiently or permanently transfected genes, or both. Gene sequences may be full or partial length, cloned or naturally occurring.

The multi-purpose substrates described herein can comprise one or more bioactive molecules that can facilitate cell adhesion to the calcium phosphate coating, promote cell function, or cell growth, or all three. In one aspect, one or more bioactive molecules are part of the composition used to produce the calcium phosphate coating. In this aspect, the bioactive molecule is dispersed uniformly throughout the calcium phosphate coating. In another aspect, once the calcium phosphate coating has been produced, the coating is contacted with one or bioactive molecules.

Bioactive molecules include human or veterinary therapeutics, nutraceuticals, vitamins, salts, electrolytes, amino acids, peptides, polypeptides, proteins, carbohydrates, lipids, polysaccharides, nucleic acids, nucleotides, polynucleotides, glycoproteins, lipoproteins, glycolipids, glycosaminoglycans, proteoglycans, growth factors, differentiation factors, hormones, neurotransmitters, pheromones, chalones, prostaglandins, immunoglobulins, monokines and other cytokines, humectants, minerals, electrically and magnetically reactive materials, light sensitive materials, anti-oxidants, molecules that may be metabolized as a source of cellular energy, antigens, and any molecules that can cause a cellular or physiological response. Any combination of molecules can be used, as well as agonists or antagonists of these molecules. Glycoaminoglycans include glycoproteins, proteoglycans, and hyaluronan. Polysaccharides include cellulose, starch, alginic acid, chytosan, or hyaluronan. Cytokines include, but are not limited to, cardiotrophin, stromal cell derived factor, macrophage derived chemokine (MDC), melanoma growth stimulatory activity (MGSA), macrophage inflammatory proteins 1 alpha (MIP-1 alpha), 2, 3 alpha, 3 beta, 4 and 5, interleukin (IL) 1, IL-2, IL-3, IL-4, IL-5, IL-6, IL-7, IL-8, IL-9, IL-10, IL-11, IL-12, IL-13, TNF-alpha, and TNF-beta. Immunoglobulins useful herein include, but are not limited to, IgG, IgA, IgM, IgD, IgE, and mixtures thereof. Amino acids, peptides, polypeptides, and proteins can include any type of such molecules of any size and complexity as well as combinations of such molecules. Examples include, but are not limited to, structural proteins, enzymes, and peptide hormones.

The term bioactive molecule also includes fibrous proteins, adhesion proteins, adhesive compounds, deadhesive compounds, and targeting compounds. Fibrous proteins include collagen and elastin. Adhesion/deadhesion compounds include fibronectin, laminin, thrombospondin and tenascin C. Adhesive proteins include actin, fibrin, fibrinogen, fibronectin, vitronectin, laminin, cadherins, selectins, intracellular adhesion molecules 1, 2, and 3, and cell-matrix adhesion receptors including but not limited to integrins such as $\alpha_5\beta_1$, $\alpha_6\beta_1$, $\alpha_7\beta_1$, $\alpha_4\beta_2$, $\alpha_2\beta_3$, and $\alpha_6\beta_4$.

The term bioactive molecule also includes leptin, leukemia inhibitory factor (LIF), RGD peptide, tumor necrosis factor alpha and beta, endostatin, angiostatin, thrombospondin, osteogenic protein-1, bone morphogenic proteins 2 and 7, osteonectin, somatomedin-like peptide, osteocalcin, interferon alpha, interferon alpha A, interferon beta, interferon gamma, interferon 1 alpha, and interleukins 2, 3, 4, 5 6, 7, 8, 9, 10, 11, 12, 13, 15, 16, 17 and 18.

The term "growth factor" as used herein means a bioactive molecule that promotes the proliferation of a cell or tissue. Growth factors useful herein include, but are not limited to, transforming growth factor-alpha. (TGF-alpha), transforming growth factor-beta. (TGF-beta), platelet-derived growth factors including the AA, AB and BB isoforms (PDGF), fibroblast growth factors (FGF), including FGF acidic isoforms 1 and 2, FGF basic form 2, and FGF 4, 8, 9 and 10, nerve growth factors (NGF) including NGF 2.5s, NGF 7.0s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), EG-VEGF, VEGF-related protein, Bv8, VEGF-E, granulocyte colony stimulating factor (G-CSF), insulin like growth factor (IGF) I and II, hepatocyte growth factor (HGF), glial neurotrophic growth factor (GDNF), stem cell factor (SCF), keratinocyte growth factor (KGF), transforming growth factors (TGF), including TGFs alpha, beta, beta1, beta2, and beta3, skeletal growth factor, bone matrix derived growth factors, and bone derived growth factors and mixtures thereof. Some growth factors can also promote differentiation of a cell or tissue. TGF, for example, can promote growth and/or differentiation of a cell or tissue. Some preferred growth factors include VEGF, NGFs, PDGF-AA, PDGF-BB, PDGF-AB, FGFb, FGFa, HGF, and BGF.

The term "differentiation factor" as used herein means a bioactive molecule that promotes the differentiation of cells or tissues. The term includes, but is not limited to, neurotrophin, colony stimulating factor (CSF), or transforming growth factor. CSF includes granulocyte-CSF, macrophage-CSF, granulocyte-macrophage-CSF, erythropoietin, and IL-3. Some differentiation factors may also promote the growth of a cell or tissue. TGF and IL-3, for example, can promote differentiation and/or growth of cells.

The term "adhesive compound" as used herein means a bioactive molecule that promotes attachment of a cell or tissue to a fiber surface comprising the adhesive compound.

Examples of adhesive compounds include, but are not limited to, fibronectin, vitronectin, and laminin.

The term "deadhesive compound" as used herein means a bioactive molecule that promotes the detachment of a cell or tissue from a fiber comprising the deadhesive compound. Examples of deadhesive compounds include, but are not limited to, thrombospondin and tenascin C.

The term "targeting compound" as used herein means a bioactive molecule that functions as a signaling molecule inducing recruitment and/or attachment of cells or tissues to a fiber comprising the targeting compound. Examples of targeting compounds and their cognate receptors include attachment peptides including RGD peptide derived from fibronectin and integrins, growth factors including EGF and EGF receptor, and hormones including insulin and insulin receptor.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in °C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the described process. Only reasonable and routine experimentation will be required to optimize such process conditions.

Preparation of Eu-Labeled Collagen

Figure 1:
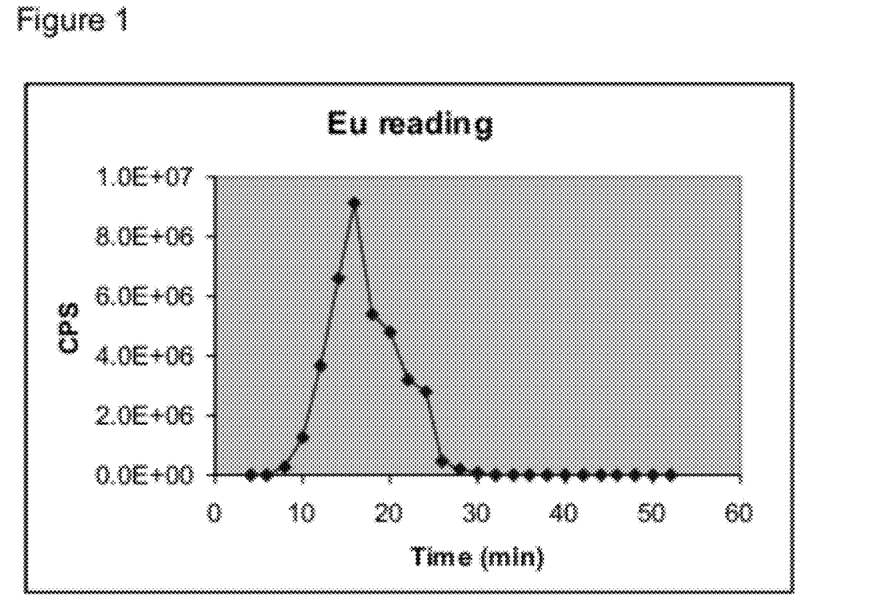
FIG. 1 shows Eu fluorescence of the collected fraction over time of Eu-labeled collagen.
Figure 2:
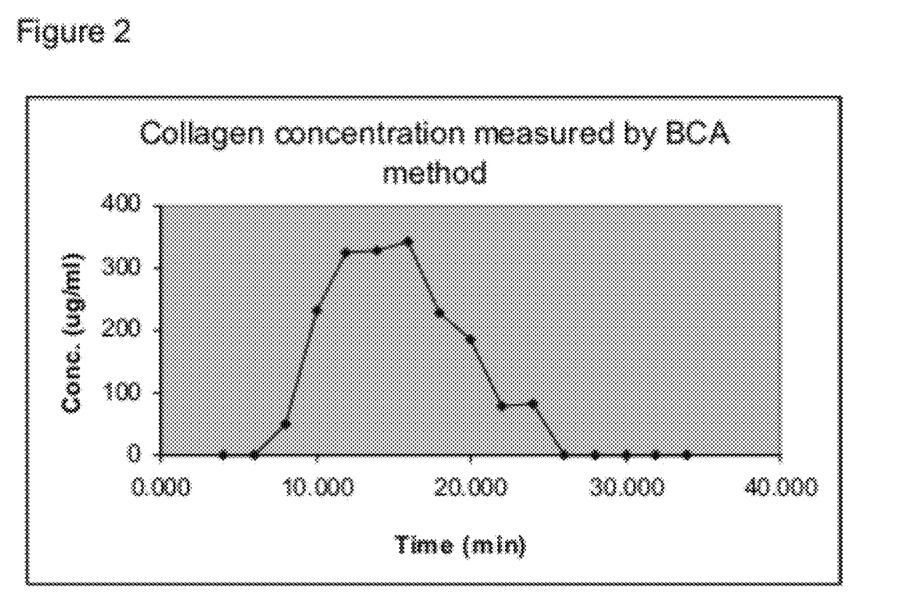
FIG. 2 shows the collagen concentration of the collected fraction over time of Eu-labeled collagen.

Collagen was labeled with Eu using a kit from Perkin Elmer (Delphia Eu-Labelling Reagent 1244-301). It was purified using Superdex200 prep grade (GE Healthcare). The labeled collagen was characterized using a BCA protein assay from Pierce (#23235). The protein was stored at −20° C. The Eu ions were covalently bound to the collagen and only the enhancement solution was able to release Eu from the collagen for measurement. FIG. 1 shows the Eu concentration of each fraction collected every two minutes and FIG. 2 shows the corresponding protein concentration. The peak fractions of collagen collected between 10 to 18 minutes had strong Eu signals. These fractions were used for further studies.

Adsorption of Eu-Labeled Collagen on COAS and TCT

The adsorption of Eu-labeled collagen was performed by immersing the Corning Osteo Assay Surface (COAS)-coated and tissue culture treated polystyrene (TCT) 96 well plates in PBS solution at room temperature for 2 hrs and subsequent washing with PBS three times. The coating concentration was 80 µg/cm$^2$.

Desorption of Eu-Labeled Collagen from Plates

Figure 3:
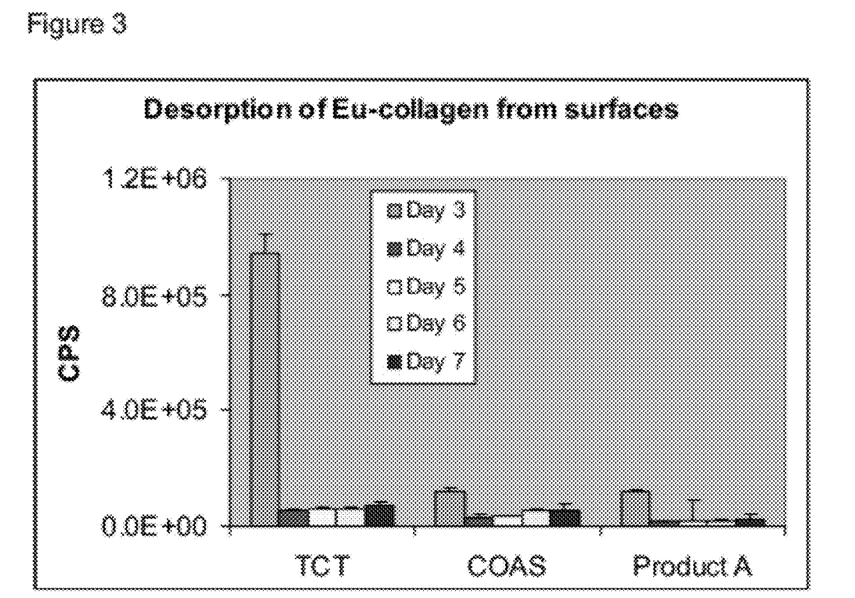
FIG. 3 shows the desorption of Eu-collagen from Corning Osteo Assay Surface (COAS) and tissue culture treated polystyrene (TCT) into the culture medium compared to europium-labeled collagen covalently attached to maleic anhydride-derivatized polystyrene plate (product A) for up to 7 days at 37° C. and with 5% $CO_2$.

Cell culture medium with serum and growth factors was added into wells with Eu-labeled collagen coated on (1) COAS and (2) TCT plates. Europium-labeled collagen covalently attached to tissue cultured treated polystyrene (product A) was used for comparison. The plates were placed in a cell culture incubator at 37° C. and with 5% $CO_2$. Three days later, the entire medium from each well was removed and fresh medium was added. From this point, no replacement of medium was performed. Every 24 hours, 5 µl of medium from each well was sampled for Eu analysis. As shown in FIG. 3, the desorption of Eu-collagen from COAS was about the same as that from product A for the first 3 days. After medium refreshment on day 3, slightly more desorption of Eu-collagen from COAS was observed compared to product A. The total accumulation of Eu-collagen in the medium of COAS was about twice that of product A on day 7. In contrast, significant desorption of Eu-collagen from the TCT surface was observed, where there was 9-fold increase in concentration compared to that of COAS on day 3. These results indicate that (1) the physical adsorption of Eu-collagen on COAS is stable; (2) a complicated chemical reaction (i.e., covalent bonding) is not necessary for Eu-collagen binding to COAS; and (3) TCT is not a suitable substrate for Eu-collagen coating with physical adsorption.

Cell Culturing and Analysis

Figure 4:
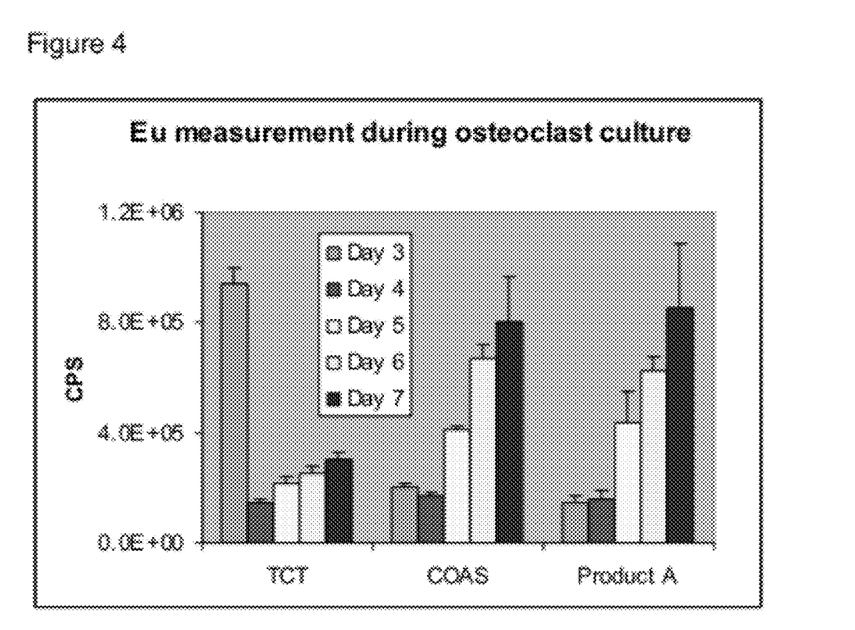
FIG. 4 shows the release of Eu-collagen into the culture medium by human osteoclast precursor cells (HOCL) seeded on the Eu-collagen coated surfaces and product A for up to 7 days.

The Eu-collagen coated COAS was used to evaluate osteoclast activity, including primary cells and cell lines. TCT plates were tested as well. Human osteoclast precursor cells from Lonza (HOCL) were used in the example. Cells were seeded at 10,000 cells/well of 96-well plate with medium containing M-CSF and RANK ligand. After 3 days, multinucleated cells started to appear on TCT surfaces, but not on COAS. At this time, the medium was refreshed to remove the basal level Eu-collagen. From this point, the medium was not changed and the release of Eu-collagen due to osteoclast activity was retained for analysis. Every 24 hr, 5 µl of medium from each well was sampled for Eu analysis. As shown in FIG. 4, the osteoclast activity profile, as measured by the release of Eu-collagen from COAS, was almost identical to that of product A from days 3 to 7. This indicates that the performance of the Eu-collagen coated COAS was as good as that of product A. On the other hand, the release of Eu-collagen from TCT was high on day 3 due to desorption but significantly lower afterwards.

Figure 5:
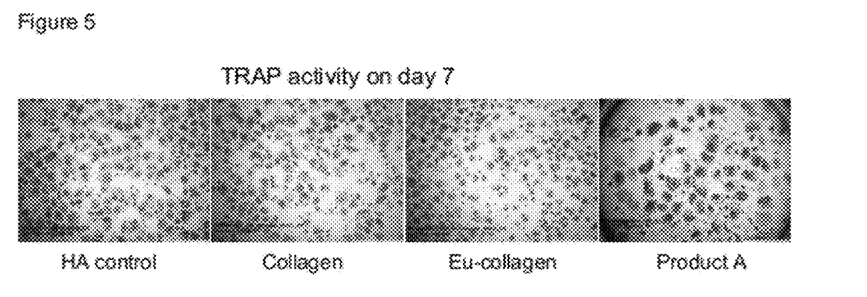
FIG. 5 shows TRAP staining of HOCL on Eu-labeled collagen coated COAS and product A surfaces after 7-day culture.
Figure 6:
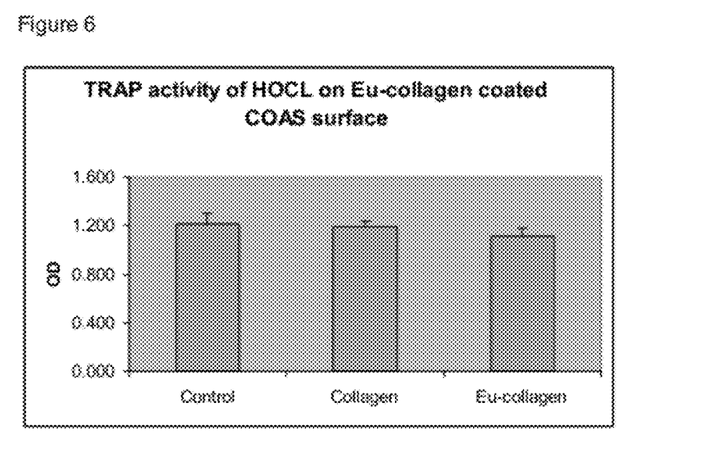
FIG. 6 shows solution based quantitative TRAP assay of HOCL on Eu-labeled collagen coated COAS and product A after 7-day culture.

TRAP (tartrate-resistant acid phosphatase) is a marker for osteoclast differentiation. After seven days of culturing, cells were fixed and stained for TRAP. Cells cultured on product A were stained for comparison. As shown in FIG. 5, there was not any visible difference in TRAP activity among the cells on collagen, Eu-collagen and control COAS surfaces, indicating that the coating did not change cell behavior. Quantitative measurement of TRAP in medium supernatant confirmed the results (FIG. 6).

Figure 7:
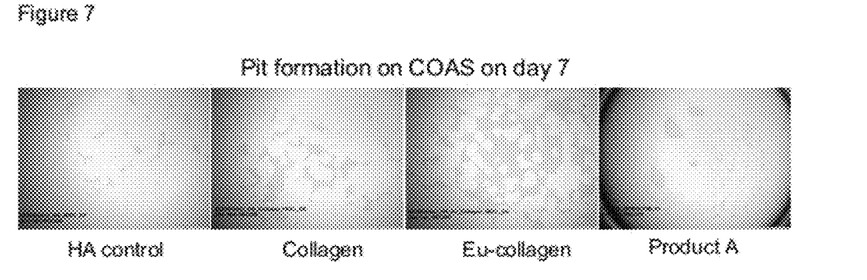
FIG. 7 shows pit formation of HOCL on Eu-labeled collagen coated COAS and product A after 7-day culture.

The osteoclast function is determined by the pit formation on the COAS plate. As shown in FIG. 7, osteoclasts were able to function well on the coated surfaces. The pit area decreased slightly on collagen and Eu-collagen coated surfaces, indicating that the protein coating might have a protective effect on the substrate that made the COAS more resistant to osteoclast resorption. Product A did not support the study of pit formation. Therefore, Eu-collagen coated COAS is superior to product A.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

What is claimed is:

1. A multi-purpose substrate comprising (1) a calcium phosphate coating on a surface of a base and (2) a fluorophore-labeled collagen adsorbed on the calcium phosphate coating.

2. The substrate of claim 1, wherein the fluorophore is a lanthanide chelate.

3. The substrate of claim 1, wherein the fluorophore is a europium chelate.

4. The substrate of claim 1, wherein the fluorophore is $Eu^{3+}$—N-(p-isothiocyanatobenzyl)diethylenetriamine-$N^1$,$N^2$,$N^3$-tetraacetic acid.

5. The substrate of claim 1, wherein the collagen is type I or type IV.

6. The substrate of claim 1, wherein the collagen is mammalian.

7. The substrate of claim 1, wherein the collagen is human collagen.

8. The substrate of claim 1, wherein the base comprises a polymer comprising polystyrene, polypropylene, polycarbonate, polyester, or any combination thereof.

9. The substrate of claim 1, wherein the base comprises an inorganic material.

10. The substrate of claim 9, wherein the inorganic material comprises glass, quartz, ceramic, silica, a metal oxide, or any combination thereof.

11. The substrate of claim 1, wherein the base comprises a microwell, dish, or flask.

12. The substrate of claim 1, wherein the calcium phosphate coating comprises hydroxyapatite or substituted hydroxyapatite.

13. The substrate of claim 1, wherein the base comprising the calcium phosphate coating is prepared by a method comprising
(a) introducing the base into a solution comprising a plurality of precursor components for producing the calcium phosphate coating;
(b) inverting the base relative to the solution; and
(c) incubating the inverted base to produce the calcium phosphate coating on the surface of the base.

14. The substrate of claim 13, wherein after step (c) exposing the calcium phosphate coating on the base to gamma irradiation.

15. A method for producing a multi-purpose substrate of claim 1, the method comprising adsorbing a fluorophore-labeled collagen to a pre-substrate, wherein the pre-substrate comprises a calcium phosphate coating on the surface of a base.

16. The method of claim 15, wherein the adsorbing step is performed at 0° C. to 40° C. from 1 to 4 hours.

17. The method of claim 15, wherein the amount of the fluorophore-labeled collagen adsorbed to the calcium phosphate coating is from 5 μg/cm² to 1 mg/cm².

* * * * *